United States Patent [19]

Webber

[11] Patent Number: 5,668,844

[45] Date of Patent: *Sep. 16, 1997

[54] SELF-CALIBRATED TOMOSYNTHETIC, RADIOGRAPHIC-IMAGING SYSTEM, METHOD, AND DEVICE

[76] Inventor: Richard L. Webber, 1240 Chester Rd., Winston-Salem, N.C. 27104-1355

[*] Notice: The term of this patent shall not extend beyond the expiration date of Pat. No. 5,359,637.

[21] Appl. No.: 326,332

[22] Filed: Oct. 20, 1994

Related U.S. Application Data

[63] Continuation of Ser. No. 875,249, Apr. 28, 1992, Pat. No. 5,359,637.

[51] Int. Cl.$^6$ ............................................. G01T 1/00
[52] U.S. Cl. .................. 378/2; 378/23; 378/162
[58] Field of Search ........................ 378/2, 23, 162, 378/163, 164

[56] References Cited

U.S. PATENT DOCUMENTS

| | | | |
|---|---|---|---|
| 4,941,164 | 7/1990 | Schuller | 378/168 |
| 5,008,947 | 4/1991 | Yamada | 378/163 |
| 5,051,904 | 9/1991 | Griffith | 378/23 |
| 5,070,454 | 12/1991 | Griffith . | |
| 5,299,254 | 3/1994 | Dancer et al. | 378/162 |
| 5,319,550 | 6/1994 | Griffith . | |
| 5,359,637 | 10/1994 | Webber | 378/2 |

FOREIGN PATENT DOCUMENTS 2016855  9/1979  United Kingdom .

OTHER PUBLICATIONS

EVS-125 X-Ray Slicer catalog, Yunihaito Co., Ltd., Shinjuku-ku, Tokoyo.

Tsuneo Saito et al., "Three-Dimensional Quantitative Coronary Angiography", IEEE Transactions on Biomedical Engineering, vol. 37, No. 8, Aug. 1990, pp. 768-777.

"Proceedings of the 14th Annual Meeting of the American Association of Physicists." vol. 17, No. 6, 26-29 Jun. 1972. Philadelphia. p. 878. R. Mohan et al. A Computer-Assisted Rapid Method for Source Localization in Interstitial Implants. abstract.

Primary Examiner—Craig E. Church

[57] ABSTRACT

A self-calibrating tomosynthetic x-ray system is provided. A calibrated device for recording radiographic images of a selected object irradiated by a source of radiation includes a first radiolucent radiographic recording medium in the form of a CCD device for recording a first projected radiographic image of the selected object. A second radiographic recording medium in the form of a CCD device is supported in fixed generally parallel position relative to the first radiographic recording medium to permit radiation from the source to pass through the first radiographic recording medium and to impinge upon the second radiographic recording medium for recording a second projected radiographic image of the selected object. A radiopaque fiducial reference in the form of a grid is supported in fixed position generally between the first and second radiographic recording mediums to permit a projected image of the radiopaque fiducial reference to be recorded on the second radiographic recording medium. Projected radiographic images of the object and the fiducial reference are then recorded at different arbitrary relative positions between the source of radiation and the object, the fiducial reference, and the recording mediums. An image of a selected object at a selected slice position through the object is synthesized from selected projected radiographic images of the object and the fiducial reference recorded by the calibrated device.

65 Claims, 6 Drawing Sheets

SELF-CALIBRATED TOMOSYNTHETIC, RADIOGRAPHIC-IMAGING SYSTEM, METHOD, AND DEVICE

This is a continuation of application Ser. No. 07/875,249, filed on Apr. 28, 1992, now U.S. Pat. No. 5,359,637.

This invention was made with government support under Contract No. 70NANBOH1070 awarded by the National Institute of Standards and Technology. The government has certain rights in the invention.

FIELD OF THE INVENTION

The present invention relates to a self-calibrating tomosynthetic, radiographic-imaging system, method, and device and, more particularly, to a calibrated radiographic-imaging device for use as part of a self-calibrating tomosynthetic X-ray system and method in which random relative positional geometries between the source of radiation and the radiographic imager affixed to the object of interest may be utilized for recording radiographic images for tomosynthesis.

BACKGROUND OF THE INVENTION

Diagnostic performance obtainable from radiographic systems is limited necessarily by sampling constraints which preclude uniform access to dynamic processes manifested in the three spatial dimensions as well as time. Conventionally, improvements in diagnostic performance have been effected by manipulation of the temporal limitations through immobilization of the object of diagnostic interest.

When temporal limitations are ignored, diagnostic performance can be enhanced through an increase in the range and number of x-ray projections produced. Early conventional bases for optimizing diagnostic performance simply involved taking multiple transmission radiographs from projection angles judged to be appropriate for the diagnostic task. When anatomical constraints precluded access to unambiguous single-projection geometries, supplemental approaches were developed involving the use of linear, circular, and hypercycloidal tomography.

A more recent improvement over conventional tomography is tomosynthesis. The primary advantage afforded by tomosynthesis over conventional tomography resides in the fact that tomosynthesis enables any number of tomographic slices to be reconstructed from a single scanning sequence of x-ray exposures. However, one of the drawbacks with the practical implementation of conventional tomosynthetic systems has been that acquisition of all tomosynthetic projections must be made with little or no movement of the irradiated tissues or objects. Only by immobilizing the object of interest is it presently possible to establish the known geometric relationships required for conventional tomosynthetic reconstruction systems.

The advent of modern computerized tomography has greatly improved diagnostic performance of conventional tomography and tomosynthesis by facilitating access to tissue or object details visible only through 2- or 3-dimensional sampling in a way that eliminates tomographic blur. However, even computerized tomography has significant shortcomings, particularly for tasks requiring high spatial resolution or the need to track tissue or object changes over extended periods of time.

Unfortunately, computerized tomography is expensive and cumbersome. Another drawback with conventional computerized tomography is that it is limited predominantly to examination of axial tissues. Computerized tomography is not easily adapted for use on extremities or breast tissues. Furthermore, computerized tomography is confined to applications which are not limited by the intrinsically low spatial resolution of computerized tomography.

Computerized tomography is also intimidating to many patients and requires nearly complete patient immobilization for relatively extended periods of time. Requiring patient immobilization over extended periods of time restricts the degree to which long-term temporal changes can be tracked. It is virtually impossible to reposition a patient in exactly the same way from one examination to another. As a result, changes in patient position tend to be confounded with tissue changes of diagnostic interest.

Similar problems are encountered with the application of conventional tomosynthesis and computerized tomography in industrial applications. The use of conventional tomosynthesis and computerized tomography is constrained. Both technologies require that the object of radiographic interest bear a fixed geometric relationship to all of the multiple projection geometries required to implement image reconstruction. Any change in projection geometry mediated by unanticipated object motion relative to the x-ray source, either during or between exposures, precludes accurate reconstruction.

A system, method, and device for self-calibrating tomosynthesis are provided by the present invention which overcome many of the constraints of conventional tomosynthesis or computerized tomography. Significantly, the need for immobilization of the irradiated object during the sequence of multiple exposures required for tomosynthetic reconstruction is eliminated. In accordance with the present invention, a calibrated radiographic imager device is affixed to the object of interest, thereby enabling the required projection geometry underlying individual projections to be determined after exposure from random or arbitrary positions of the x-ray source relative to the object of interest and the radiographic imager.

SUMMARY OF THE INVENTION

In accordance with the present invention, a method and system are provided for synthesizing an image of a selected object at a selected slice position through the selected object from a plurality of projected radiographic images of the selected object. At least one radiographic recording means is provided for recording radiographic images of the selected object. At least one fiducial reference is held in fixed position relative to the recording means so that the fiducial reference is maintained at a fixed, predetermined distance from the recording means.

Positioning means serves to maintain the selected object of radiographic interest in fixed position relative to the recording means and the fiducial reference. For this purpose, any type of holder may be utilized to fasten or attach the recording means and the fiducial reference in fixed position relative to the selected object of interest.

At least one source of radiation is provided for irradiating the selected object to enable projected radiographic images of the object and the fiducial reference to be recorded on the recording means. Depending on the particular application, the source of radiation may be, for example, either a portable or a stationary x-ray source.

In order to obtain radiographic images of the selected object at different orientations, the relative positions between the source of radiation and the object, the fiducial reference, and the recording means are varied. Projected radiographic images of the object and the fiducial reference are then recorded on the recording means at different arbitrary or random relative positions between the source of radiation and the object, the fiducial reference, and the recording means. An image synthesizer is provided for synthesizing an image of the selected object at a selected slice position through the object from selected projections of the radiographic images of the object and the fiducial reference recorded on the recording means.

For synthesizing an image at a selected slice location, the location of the projected image of the fiducial reference at a plane at the recording means is determined for each selected projection. A reference location at the plane of the recording means is then selected for the selected set of image locations of the fiducial reference recorded on the recording means. For example, the reference location may be selected as the center of gravity of the selected set of image locations of the fiducial reference. For each selected projection, the distance and path of each projected image of the fiducial reference from the selected reference location is then determined. Next, for each selected projection, the respective location of the projected image of the fiducial reference at the selected slice position is determined in such a way that the position of the projected image of the fiducial reference for each selected projection coincides with the selected reference location for a predetermined slice position through the fiducial reference. Accordingly, the projected images of the fiducial reference for the selected projections will uniformly converge toward or diverge from the selected reference location depending on the selected relative slice position for the synthesized image.

For each selected projection, the projected image of the object and the fiducial reference recorded on the recording means is then shifted to the selected slice position so that the projected image of the fiducial reference recorded on the recording means moves for each selected projection to its respective location at the selected slice position. After shifting to the selected slice position, the projected images of the object and the fiducial reference are spatially averaged to generate a tomosynthetic slice. The spatially averaged image may also be optionally filtered in a task-dependent manner.

In accordance with the present invention, a self-calibrated device for recording radiographic images of a selected object irradiated by a source of radiation is also provided. The device includes a radiographic recording medium for recording a projected radiographic image of the selected object. A radiopaque fiducial reference is provided for positioning between the recording medium and the source of radiation to enable a projected image of the radiopaque fiducial reference to be recorded on the recording medium together with the projected image of the selected object. In order to calibrate the device, a holder is provided for holding the fiducial reference in fixed position relative to the recording medium. Thus, the holder functions to maintain the radiopaque fiducial reference at a fixed predetermined distance from the recording medium.

In an alternate configuration, the device includes a support and a first radiolucent radiographic recording medium, such as a CCD device, supported on the support for recording a projected radiographic image of the selected object. A second radiographic recording medium, such as a second CCD device, is supported relative to the support in fixed position relative to the first radiographic recording medium. The second radiographic recording medium is supported at a selected orientation relative to the first radiographic recording medium to permit a radiographic image to be recorded on the second recording medium. In a specific arrangement, the second radiographic recording medium is positioned relative to the first radiographic recording medium so that radiation from the source of radiation passes through the first radiographic recording medium and impinges upon the second radiographic recording medium to record a second projected radiographic image of the selected object. To facilitate projection geometries, the first and second radiographic recording mediums may be oriented in parallel with each other.

A radiopaque fiducial reference, such as a uniform grid, is supported relative to the support at a fixed position relative to the second recording medium so that a projected radiographic image of the fiducial reference is recorded on the second recording medium. In a specific arrangement, the fiducial reference is supported in fixed position generally between the first and second radiographic recording mediums to permit a projected image of the radiopaque fiducial reference to be recorded on the second radiographic recording medium together with a second projected radiographic image of the selected object.

The radiopaque fiducial reference includes an indicator for indicating a selected size and a selected position on the fiducial reference so that the projected image of the fiducial reference recorded on the second recording medium can exhibit a different size relative to the selected size of the indicator on the fiducial reference and a displacement to a different position relative to the selected position of the indicator on the fiducial reference. The indicator may also include a frequency indicator for exhibiting a selected frequency pattern at the fiducial reference so that the projected image of the fiducial reference recorded on the second recording medium can exhibit a different frequency pattern relative to the selected frequency pattern at the fiducial reference as well as a phase shift relative to the selected frequency pattern at the fiducial reference.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE PREFERRED EMBODIMENTS

Figure 1:
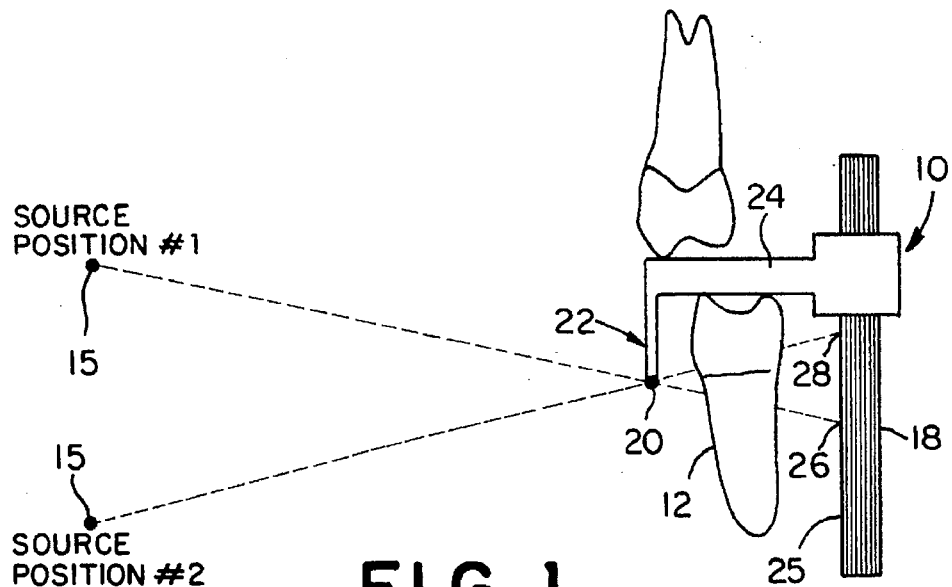
FIG. 1 is a schematic representation of a self-calibrating tomosynthetic x-ray system employing a calibrated radiographic recording device in accordance with the present invention.

Referring to FIG. 1, a self-calibrating tomosynthetic radiographic-imaging system is depicted in which a calibrated detection device generally designated 10 is employed for recording radiographic images of a selected object in the form of a tooth 12 irradiated by an arbitrarily positioned point source of radiation 15 such as a point source of x-rays. The detection device 10 includes a radiographic recording medium 18 for recording a projected radiographic image of the selected object 12. The radiographic recording medium 18 may be in the form of a radiation-sensitive, solid-state image detector such as a radiolucent charge-coupled device (CCD). The CCD may be of the type currently manufactured by English Electron Valve of Great Britain for use in an intra-oral x-ray system marketed by Regam Medical System A.B. of Sundsvall, Sweden.

A single radiographic fiducial reference object 20 in the form of a small metallic bead is positioned conveniently between the source of radiation 15 and the image detector 18 to enable a projected image of the radiopaque fiducial reference object 20 to be recorded on the image detector 18 together with the projected image of the selected object 12. The fiducial reference object 20 serves to indicate a reference size and position for comparison to the size and position of the projected image of the fiducial reference object recorded on the image detector 18.

The detector device 10 includes a rigid radiolucent holder 22 for holding the radiopaque fiducial reference object 20 in fixed position relative to the image detector 18 so that the fiducial reference is always maintained at a fixed predetermined distance from the image recording surface 25 of the image detector. As shown in FIG. 1, the holder includes an object mounting portion 24 which permits the detector device 10 to be rigidly mounted with respect to the selected object 12 to hold the image detector 18 and the radiopaque fiducial reference object 20 in fixed position relative to the selected object 12. As shown in FIG. 1, the object mounting portion 24 of the holder may be securely gripped between the teeth being radiographed.

The object mounting portion 24 of the holder 22 enables the detector device 10 to be mounted in fixed position with respect to the selected object, i.e., tooth 12, so that the selected object is positioned intermediate the radiopaque fiducial reference object 20 and the image detector 18. In an alternative arrangement, the holder 22 could function to position the fiducial reference object 20 between the selected object of interest 12 and the image detector so long as a known fixed distance is maintained between the fiducial reference object 20 and the active recording surface of the image detector 18.

As shown in FIG. 1, the fiducial reference object 20 is conveniently positioned in front of the image detector 18 so that the projection of the fiducial reference object may be recorded on the active surface of the image detector at different positions of the x-ray source 15. For example, when the x-ray source is located at source position #1, the projection of the fiducial reference object 20 is recorded on the active surface 25 of the image detector at position 26. Likewise, when the x-ray source 15 is located at source position #2, the projection of the fiducial reference object 20 is recorded on the active surface 25 of the image detector 18 at position 28. For arbitrary positions of the x-ray source 15, the projections of diagnostic interest also contain projections of the radiopaque fiducial reference object 20. Accordingly, the relative displacement measurements required for tomosynthetic registration can be read from the same images that contain the disparate radiographic projections required for tomosynthetic reconstruction.

Figure 2:
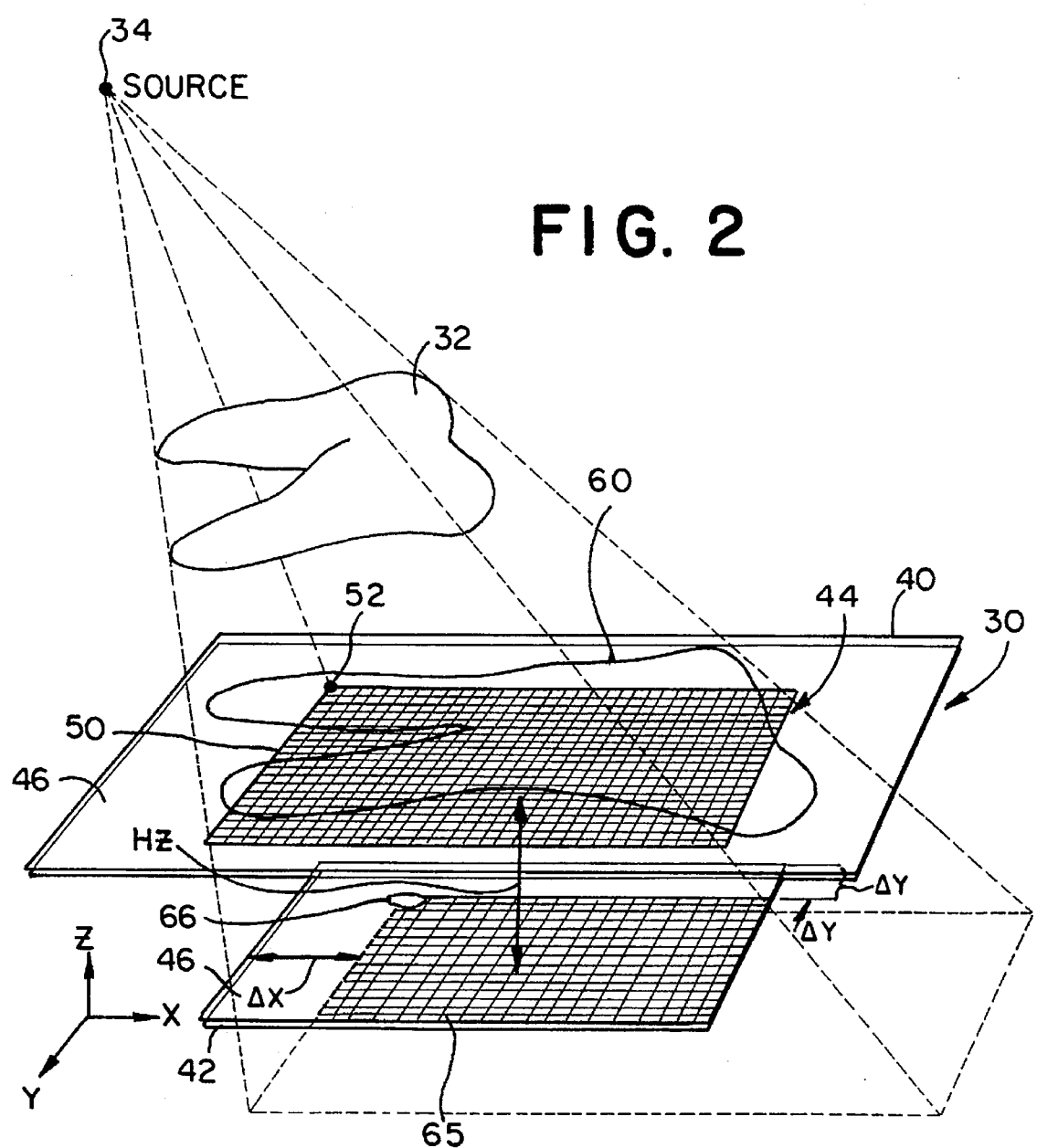
FIG. 2 is a schematic representation of a self-calibrating tomosynthetic x-ray system employing a calibrated radiographic recording device in accordance with another preferred embodiment of the present invention.
Figure 8:
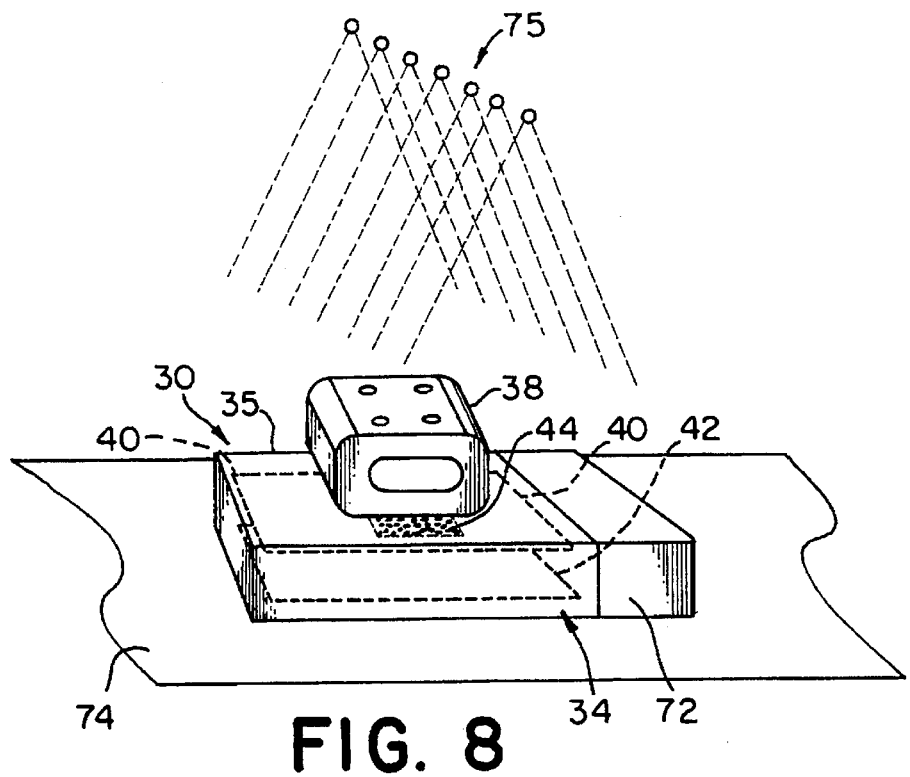
FIG. 8 is a schematic representation of a self-calibrating tomosynthetic x-ray system using a calibrated radiographic recording device of the type schematically shown in FIG. 2 in which a conveyer belt moves an object of interest resting upon the radiographic recording device relative to a series of point radiation sources.
Figure 9:
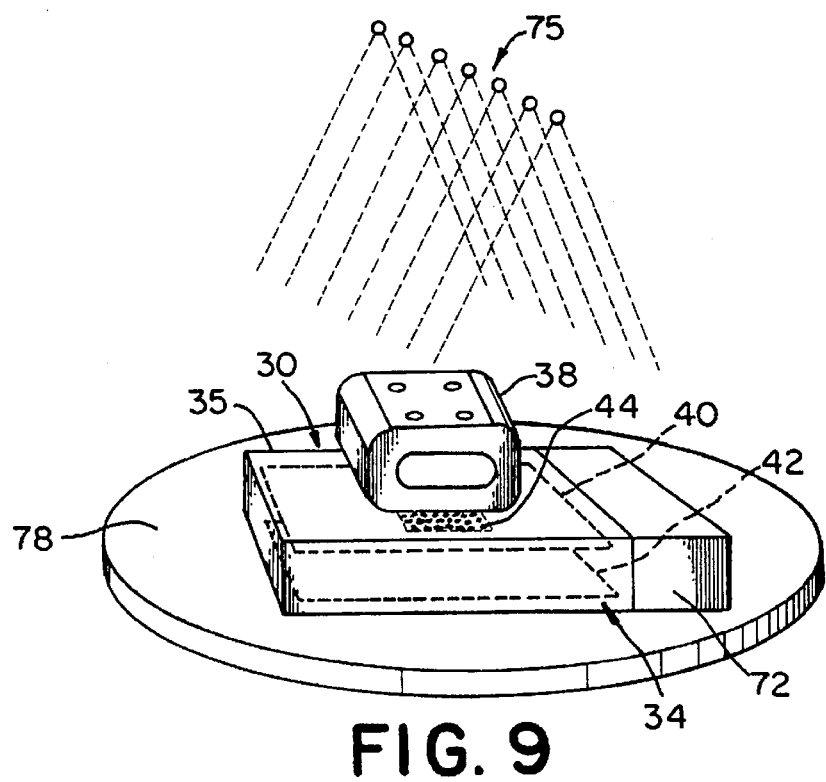
FIG. 9 is a schematic representation of a self-calibrating tomosynthetic x-ray system using a calibrated radiographic recording device of the type schematically shown in FIG. 2 in which a rotatable turntable moves an object of interest resting upon the radiographic recording device relative to a series of point radiation sources.

Referring to FIG. 2, a self-calibrating tomosynthetic x-ray system employs a calibrated detector device, generally designated 30, having a different configuration from the detector device 10 depicted in FIG. 1. Detector device 30 functions to record radiographic images of a selected object 32, such as a tooth, irradiated by a distant, arbitrarily positioned point source of radiation 34 such as an x-ray source. As best shown in FIGS. 8 and 9, the detector device 30 includes a support casing 34 having at least a radiolucent surface 35 to which the object of interest 38 may be secured or mounted. A first radiolucent radiographic recording medium 40 is supported in fixed position relative to the support casing for recording a first projected radiographic image of the selected object. A second radiographic recording medium 42 is supported relative to the support casing 34 in fixed position relative to the first radiographic recording medium 40 and at a selected angle of orientation relative to the first radiographic recording medium 40 to permit radiation from the source of radiation 34 to pass through the first radiographic recording medium and impinge upon the second radiographic recording medium for recording a second projected radiographic image of the selected object. As shown in FIGS. 1, 8 and 9, a radiopaque fiducial reference, generally designated 44, is supported relative to the support casing at a fixed position generally between the first and second radiographic recording mediums 40 and 42 to permit a projected image of the radiopaque fiducial reference 44 to be recorded on the second radiographic recording medium.

Preferably, the first and second radiographic recording mediums 40 and 42 are in the form of solid-state, radiation-sensitive image detectors such as radiolucent charge-coupled devices (CCDs). Each image detector 40 and 42 includes a generally flat, radiation-sensitive active surface 46 which serves as a detector plane for recording radiographic images. As shown in FIG. 2, the image detectors 40 and 42 are positioned so that the active surfaces 46 of the image detectors 40 and 42 are disposed generally parallel with one another. The parallel arrangement of the active surfaces 46 of image detectors 40 and 42 simplifies the projection geometries.

The radiopaque fiducial reference 44 includes a radiopaque grid 50 which is attached to the underside of image detector 40. The radiopaque grid 50 is secured to the underside of the first image detector so that the grid is held in fixed position relative to the active surfaces 46 of first and second image detectors 40 and 42. The radiopaque grid 50 is positioned generally parallel with respect to the active surfaces 46 of the first and second image detectors 40 and 42 and is disposed at a fixed, predetermined distance Hz from the active surface 46 of the second image detector 42. The radiopaque grid 50 functions as a frequency indicator for exhibiting a selected frequency pattern at the fiducial reference. The grid 50 includes any desired radiopaque pattern. For example, as shown in FIG. 2, the grid 50 includes uniform, cyclical, orthogonally patterned radiopaque linings at one selected frequency pattern of spacing. However, the grid may also include non-uniformly spaced, orthogonally patterned radiopaque linings to produce a frequency pattern having different frequencies of spacing. In the most general case, the grid may be characterized by an asynchronous two-dimensional pattern having a spatial frequency distribution pattern characterized by the term white noise, i.e., all spatial frequencies are indicated with equal modulation. The most suitable configuration of the grid pattern depends on the particular application. The fiducial reference 44 may also include a radiographic fiducial reference object 52 such as a metallic bead affixed at a selected position to the underside of the first image detector 40. The bead 52 functions as a displacement indicator at the fiducial reference for indicating a selected size and position of the fiducial reference.

As shown in FIG. 2, the radiation from the source 34 first passes through the selected object 32 of diagnostic interest, then through the first image detector 40 to produce a radiographic image 60 of the selected object on the active surface 46 of the image detector 40. The radiation then passes through the radiolucent image detector 40 and impinges on the fiducial reference 44 in the form of the fiducial reference grid 50 and the fiducial reference object 52 affixed to the underside of the first image detector 40. Because the fiducial reference 44 is positioned beyond the active surface 46 of the first image detector 40, the effect of the fiducial reference on the image produced by the first image detector 40 is negligible.

The grid 50 is made from a highly radiopaque material such as metal wire. Consequently, when the grid is exposed by source x-rays penetrating the first image detector 40, the grid 50 produces a uniform, high contrast, cyclical, orthogonally patterned radiographic projection 65 on the active surface 46 of the second image detector 42. The projected image of the grid onto the active surface of the second image detector enables such image to be recorded by the second image detector. The frequency pattern of the recorded image may be enlarged and displaced relative to the frequency pattern of the grid itself.

Likewise, the fiducial reference bead 52 attached to the underside of the first image detector 40 may create an enlarged and displaced projected image 66 on the active surface 46 of the second image detector 42. The enlarged and displaced image of the selected object 32 is recorded by the second image detector 42. Since one of the primary purposes of the second image detector 42 is to detect displacement and magnification of the fiducial reference grid 50 and/or the fiducial reference bead 52, the second image detector 42 may be optionally smaller than the first image detector 40.

The use of the second image detector 42 together with a fiducial reference 44 positioned at a fixed predetermined distance from the active surface 46 of the second image detector 42 enables the detector device 30 to generate sufficient data to reflect its position after exposure relative to the x-ray source 34 for each recorded projection. The relative positioning of the detector device 30 with respect to the x-ray source 34 may be determined either by frequency domain analysis of the image produced on the active surface of the second image detector 44 by the radiopaque grid rigidly attached to the non-active underside of the first image detector or by spatial domain analysis of the image or images produced on the active surface of the second image detector by selected portions of the radiopaque grid or by the fiducial reference bead 52 attached to the underside of the first image detector 40.

Because the second image detector 42 is located farther from the source 34 than is the first image detector 40, the projected image 65 of the grid 50 exhibits a different frequency pattern relative to the actual frequency pattern exhibited by the grid 50 itself. The spatial frequency of the oscillations recorded by the second image detector 42 will be necessarily lower than the frequency of oscillations of the grid 50 itself. This change in spatial frequency can be used to provide an indication of associated magnification.

Magnification can be determined from the predetermined distance Hz separating the grid 50 from the imaging surface 46 of the second image detector 42 and the unknown distance Sz along the z axis separating the grid 50 from the source 34. The magnification formula is:

$$M=(Sz+Hz)/Sz$$

Where

M=magnification

Hz=the predetermined fixed distance separating the fiducial reference grid from the active surface of the second image detector Sz=the unknown distance of separation between the radiation source and the fiducial reference along the z-axis.

From the magnification formula, the distance Sz can be derived as follows:

$$Sz=Hz/(M-1)$$

What remains in order to locate the relative positions of the source of radiation from the image data, as is necessary for the tomosynthetic reconstruction of images, is the determination of projected positions of image data in selected planes parallel to the active surfaces 46 of the image detectors 40 and 42. The amount of displacement of the recorded image 65 of the fiducial reference grid 50 relative to the position of the actual grid itself can be ascertained from the phase shift exhibited by the recorded image cf the grid pattern relative to the actual grid pattern. The phase difference between the actual grid pattern and the projected image of the grid pattern can be determined through 2-dimensional Discrete Fourier Transformations of the original grid pattern and a demagnified off-axis projection image of the grid pattern. An inverse transformation of the phase difference from the frequency domain will reflect positions of amplitude peaks in the spatial domain which are displaced by the respective shift distances. The determination of the phase shift permits localization of the x-ray source 34 relative to the spatially linked object 32 and the detector device 30.

In the spatial domain, the change in size of the projection of the fiducial reference relative to the actual size of the fiducial reference reflects magnification. For example, the change in size of the projected image 66 of the fiducial reference bead 52 relative to the actual size of the bead 52 serves as a size displacement indicator which provides an indication of magnification. Likewise, the change in size of the projected image 65 of the fiducial grid relative to the actual grid size also provides an indication of magnification. In order to determine the angulation of the x-ray source, the position of the projected image of the fiducial reference bead 66 can be compared to the actual position of the bead 52 itself. Similarly, the position of the projected image of the grid 65 can be compared to the actual position of the grid 50 itself to determine angulation. Comparison of the position of the image of the fiducial reference with respect to the actual position of the fiducial reference serves as a position displacement indicator which yields a displacement of $\Delta x$ in the x direction and a displacement of $\Delta y$ in the y direction as best shown in FIG. 2.

The frequency-domain approach has an advantage in that the data contributing to the associated measurements are distributed across a large portion of the active surface 46 of the second image detector 42. Distributing the contributing data across the active surface of the second image detector averages out the effects of any site-specific artifacts, thereby making the measurement process less prone to the effects of irrelevant x-ray patterns contributing to the composite image recorded on the active surface of the second image detector 42. For example, x-ray patterns which are irrelevant to the recorded image of the fiducial reference are caused by contributions produced by the irradiated object itself and the structural elements intrinsic to the first image detector 40. On the other hand, the spatial-domain approach has the advantage of mathematical and conceptual simplicity. In addition, the spatial-domain approach does not require much active surface 46 on the second image detector 42 because all required image translation data can be produced from projections of a single reference point, i.e., fiducial reference bead 52.

An advantage in utilizing a detection device 30 having a pair of parallel image detectors 40 and 42 is that the projection on the active surface 46 of the first image detector 40 is necessarily correlated to a high degree with the image produced on the second image detector 42. With the pair of image detectors 40 and 42, the selected object is in effect radiographed twice. With appropriate processing and suppression of known artifacts such as this image data contributed by the fiducial reference and the characteristics of the first image detector 40, image data for the selected object obtained from the second image detector 42 can be used to improve the data obtained from the first image detector 40.

In order to obtain image data from which tomosynthetic reconstruction can be effected, it is important that the selected object be maintained in a fixed position relative to the fiducial reference 44 and the image detectors 40 and 42 during radiation exposures. So long as the stability is maintained between the detector device 30 and the irradiated structures of interest, tomosynthetic slices can be produced from projections generated from any angle in any position and in any sequence.

Moving objects can be analyzed by affixing the image detector 30 to the moving object so long as the time required for individual exposure is short compared to the movement of the object per unit time. A fixed, field emission x-ray machine capable of producing extremely short bursts of high-energy x-rays may be used to produce a series of radiographic projections, each bearing a different angle relative to the source because of the movement of the irradiated structure between successive exposures. The movement of the selected object together with the attached detector device 30 relative to the x-ray source creates the angular disparity required for tomosynthesis. As such, the system can be used with severely afflicted Parkinsonian patients and others prone to involuntary movement since there are no constraints on the nature of the movement of the irradiated object so long as the detector device can be held in fixed position relative to the object by securing the detection device to the object, and any such movement remains relatively slow with respect to the exposure time required per projection.

The system may also be used for sequential analysis of structures having cyclical movement, such as a beating heart. For applications of this nature, short x-ray bursts are synchronized by a trigger circuit linked to a particular part of the cardiac cycle. Such synchronization, in effect, maintains the relative fixed position of the irradiated object with respect to the detector device during exposures.

The detector device 30 can also be used in industrial applications for purposes of nondestructive testing of a selected object 38. For example, the detector device 30 can be used to detect fatigue cracks or other flaws in various critical structures. As shown in FIGS. 8 and 9, the selected object of interest 38 is placed upon the detector device 30 so that the selected object 38 remains in fixed position relative to the detector device 30. The detector device 30 includes the parallel stacked image detectors 40 and 42 supported within a sealed and calibrated radiolucent casing 34. The fiducial reference 44 is supported relative to the casing 34 generally between the image detectors 40 and 42. The detector device 30 may include a transmitter 72, such as an optional radio, infrared, or other type of transmitter, to permit remote-control data transfer from the detector device 30.

As shown in FIG. 8, the selected object of interest 38, together with the detector device 30, is placed as a unit on a movable conveyer belt 74 which functions to move the selected object 38 and the detector device 30 relative to the radiation source 75. The radiation source 75 includes a plurality of point-radiation sources which can be activated independently and in multiples as the selected object 38 together with the detector unit 30 moves along the conveyer. Similarly, as shown in FIG. 9, the selected object 38, together with the detector device 30, is placed as a unit on a rotatable turntable 78 which functions to rotatably move the detector device 30 and the selected object 38 as a unit with respect to the source of radiation 75. The radiation source 75 may be in the form of a plurality of point radiation sources which can be activated independently and in multiples. The activation of different point radiation sources serves to create additional relative movement of the x-ray source relative to the selected object 38 and the detector unit 30.

As the selected object 38 and the detector device 30 move relative to the radiation source 75, projected radiographic images of the selected object 38 are recorded on image detector 40 while radiographic images of both the selected object and fiducial reference are recorded on the second image detector 42. The images are recorded at different, arbitrary relative positions between the source of radiation 75 and the selected object 38, the fiducial reference 44, and the image detectors 40 and 42. The series of projected radiographic images of the object and the fiducial reference recorded by the detector device 30 permit tomosynthetic reconstruction of an image of the selected object at a selected slice position through the object.

Figure 3:
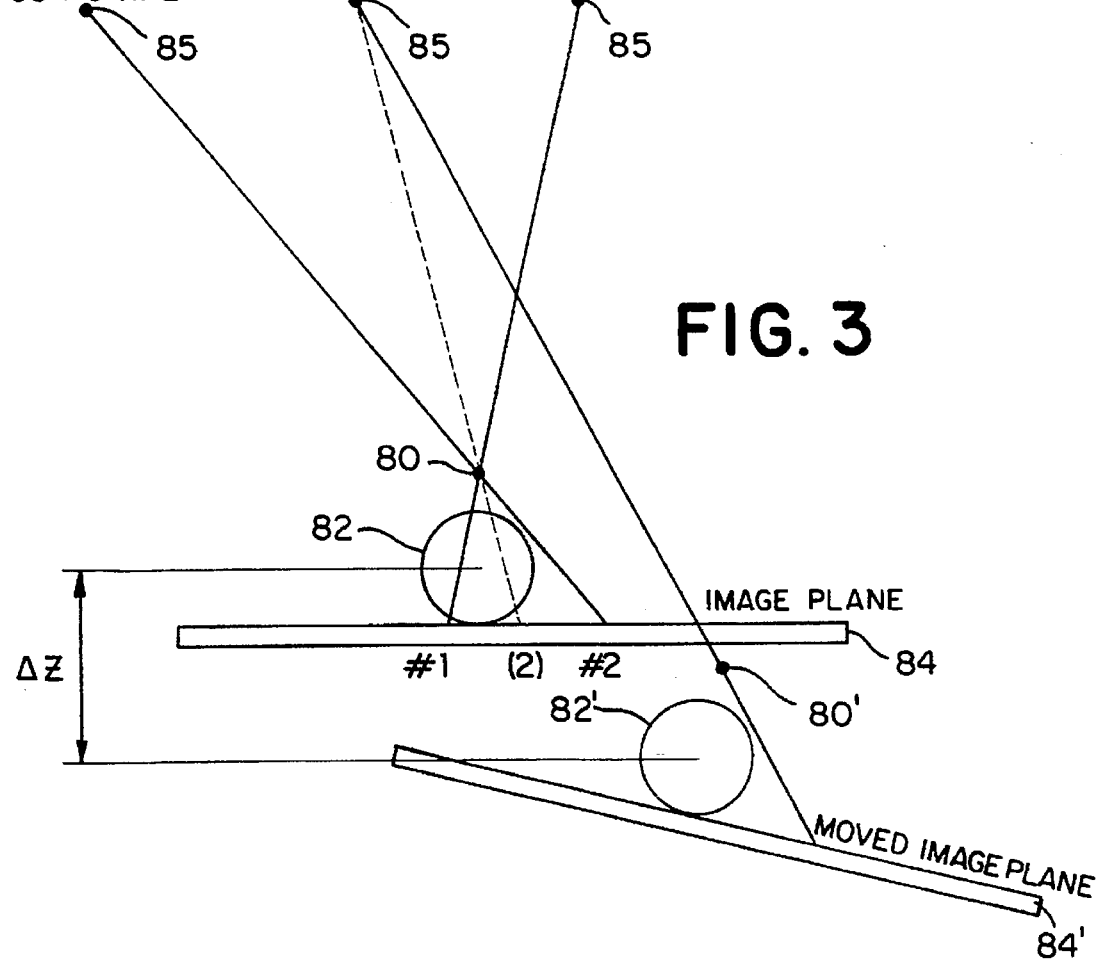
FIG. 3 is a diagram representing the use of equivalent projection geometry as a basis for compensating for a change in object position relative to an x-ray source during a tomosynthetic scan sequence.

As shown in FIG. 3, equivalent projection geometry can be used to compensate for a change in object position during a tomosynthetic scan sequence in order to obtain a locus of image projection of a single fiducial reference point within the same image plane. For relatively long focal-object distances, the effect of small displacements $\Delta z$ of the selected object on image magnification is relatively minimal.

Referring to FIG. 3, a fiducial reference object 80 is held in fixed position relative to the selected object 82 of interest and relative to the image plane 84 representing the active surface of an image detector such as a CCD. A radiation source 85 located at actual source position #1 creates a projected image of the fiducial reference 80 at position #1 on image plane 84. If the radiation source 85 is moved to actual source position #2 without any movement of the image plane 84, the radiation source 85 will produce a projected image of the fiducial reference 80 at position (2) on image plane 84. However, if the image plane 84 is moved to the position of the moved image plane 84', the fiducial reference 80 moves in position to the moved fiducial reference position 80' and the selected object 82 moves in position to the moved object position 82'. When the moved arrangement is exposed to radiation from the radiation source 85 located at actual source position #2, the projected image of the moved fiducial reference 80' is recorded on the moved image plane 84' at a position which is geometrically equivalent to the #2 position on the original image plane 84 for a radiation source 85 located at equivalent position #2. Consequently, movement of the image plane 84 together with the selected object 82 and the fiducial reference 80 creates an acceptable image on the image plane for tomosynthetic reconstruction based upon an equivalent positioning of the x-ray source to provide equivalent projection geometry.

Figure 4:
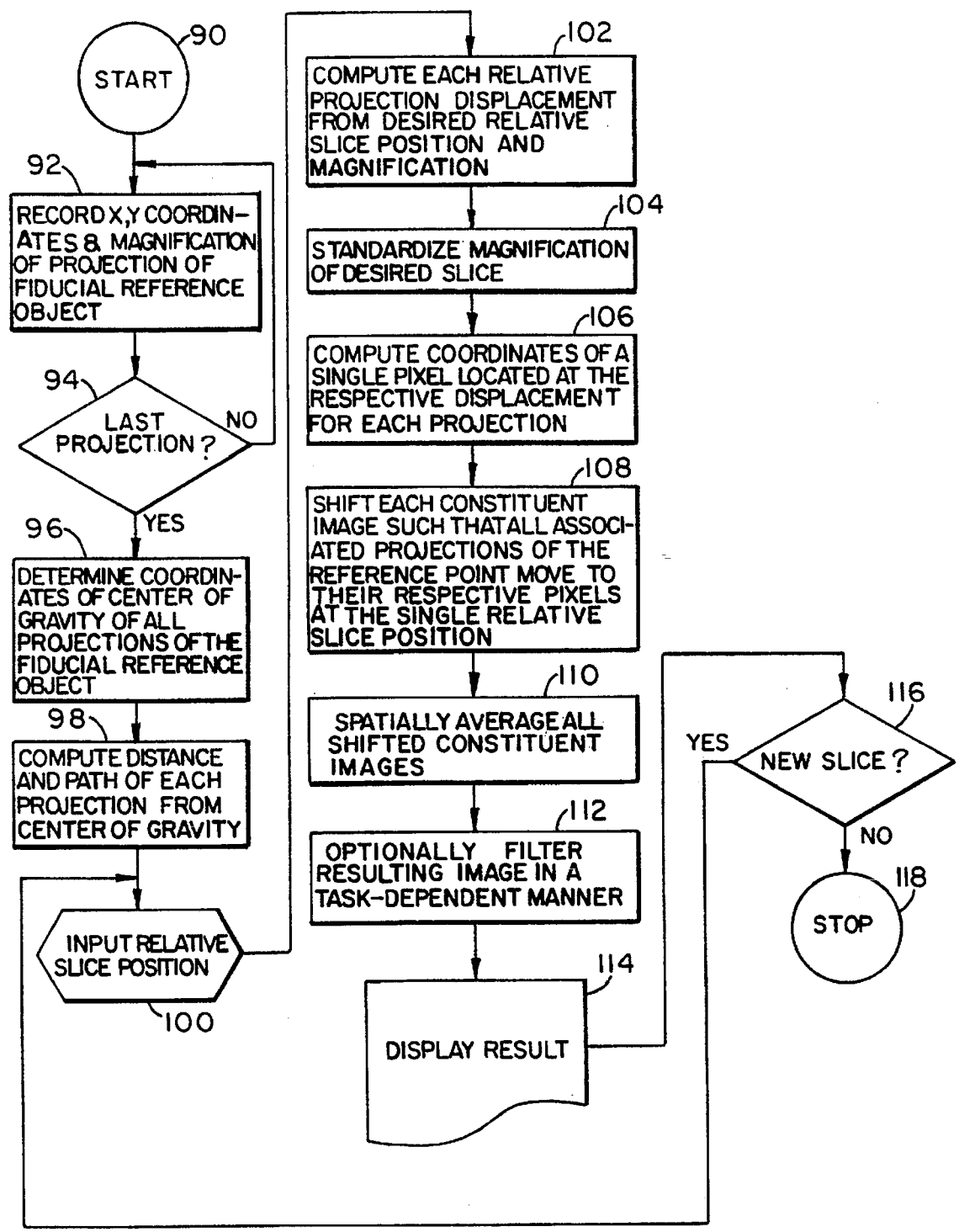
FIG. 4 is a flow chart of a method and system in accordance with the present invention for producing a synthesized image of an object at a selected slice position from a plurality of recorded radiographic images of the selected object and a fiducial reference.

Tomosynthetic reconstruction of a selected slice through the selected object of interest can be made from the selected arbitrary projections of images of the fiducial reference and the selected object recorded by the detector device 30. As shown in FIG. 4, the tomosynthetic reconstruction process starts at step 90. Each step of the tomosynthetic reconstruction may preferably be performed as part of a computer-executed process.

At step 92, the relative location of the projected image of a fiducial reference point at a plane corresponding to the active surface of the recording medium is determined for a selected projection. The X-Y coordinates of the projection image of a single fiducial reference are recorded. In addition, the magnification of the projection image of the fiducial reference at the plane is also determined and recorded. For relatively long focal-object distances, the effects of magnification are minimal. In applications in which the detector device 30 engages, or is in close proximity to, the selected object of interest, when the distance between the x-ray source and the fiducial reference grid becomes relatively large compared to the distance between the fiducial reference grid and the detector plane of the second imaging device 42, the effects of magnification become negligible and may be ignored.

After the X-Y coordinates and the magnification of the selected projection are recorded in step 92, the process at step 94 queries whether there are any additional projections. If additional projections are selected for input, the process reiterates step 92 to record the X-Y coordinates and the magnification for each selected projection. When the last selected projection is reached at step 94, the process proceeds to step 96 for purposes of determining a selected reference location for the locus of projection points from all selected projections of the fiducial reference object on the detector plane of the recording medium. For example, the process at step 96 determines the coordinates of the center of gravity of all recorded projection points of the single fiducial reference object.

Figure 5:
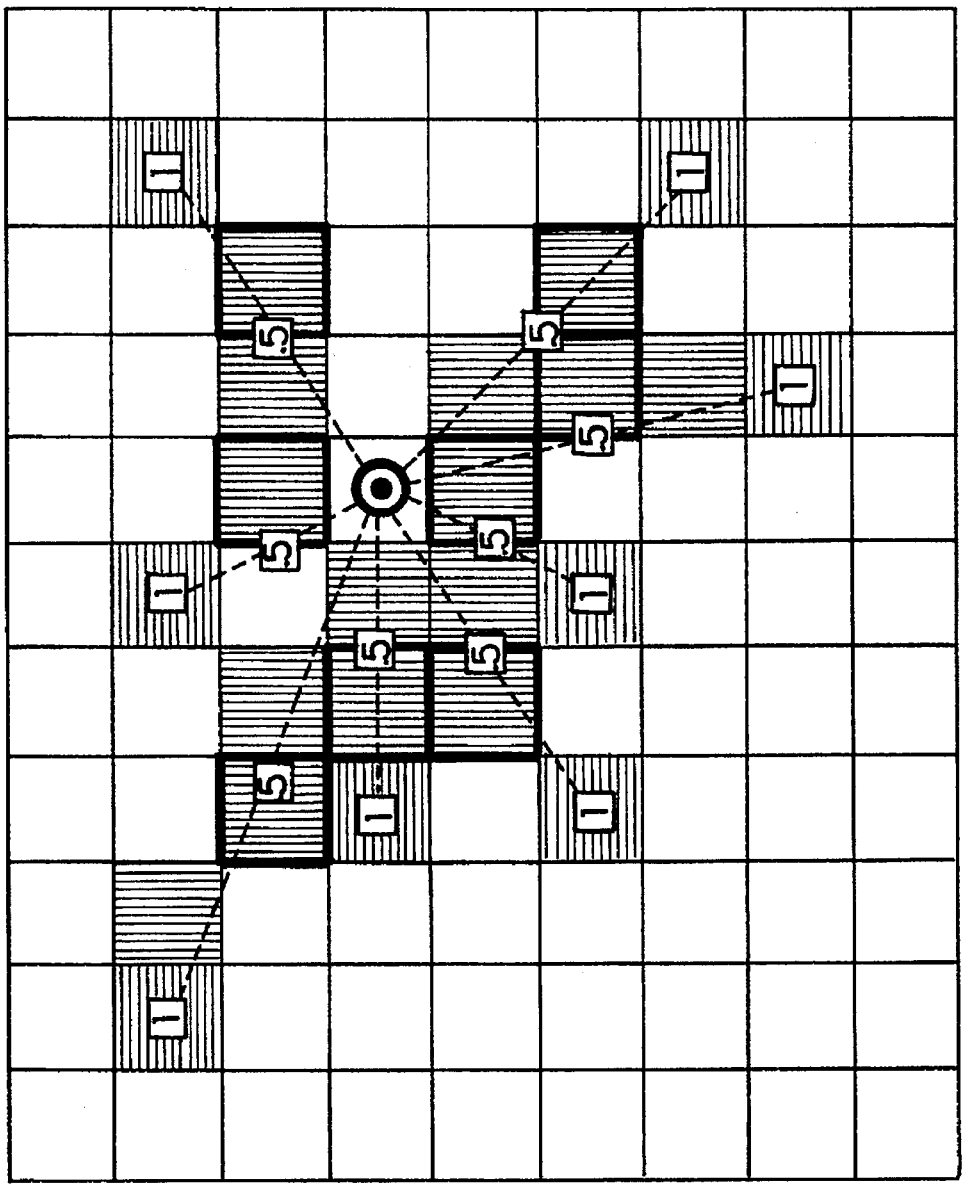
FIG. 5 is a graphic illustration of position tracking of an initial locus of projections of a single fiducial reference point relative to a selected reference point for purposes of tomosynthetic reconstruction of an image at a selected slice position.

Referring to FIG. 5, the small squares labelled 1 correspond to the initial locus of projection points of the single fiducial reference at the detector plane of the image detector. The square containing the circular target lies at the center of gravity of the distribution of the small squares labelled 1. The square containing the circular target represents the point of uniform convergence of the small squares labelled 1 as such small squares collapse uniformly toward the target position in the center of the distribution.

At step 98, the distance and path of each initial projection point of the fiducial reference from the center of gravity is determined. The distance and path of each initial projection point from the center of gravity is represented by the dotted lines shown in FIG. 5 passing from the square containing the target to the small squares labelled 1 representing the initial locus of projection points of the single fiducial reference.

At step 100, the relative slice position for the synthesized image is input. The selected slice position through the object is input as a relative slice position representing the distance of the desired slice from the detector plane relative to the distance of the fiducial reference from the detector plane.

At step 102, the relative projection displacement of each selected projection is determined on the basis of the desired relative slice position and the determined magnification of the fiducial reference object. Relative projection displacement provides a scalar correction factor for projections based on finite focal-object distances to permit the projection image to be shifted to proper location at the relative slice position. When the distance from the source to the fiducial reference grid is relatively large with respect to the distance from the fiducial reference grid to the detector plane, the effects of relative projection displacement are negligible and may be ignored.

Figure 6:
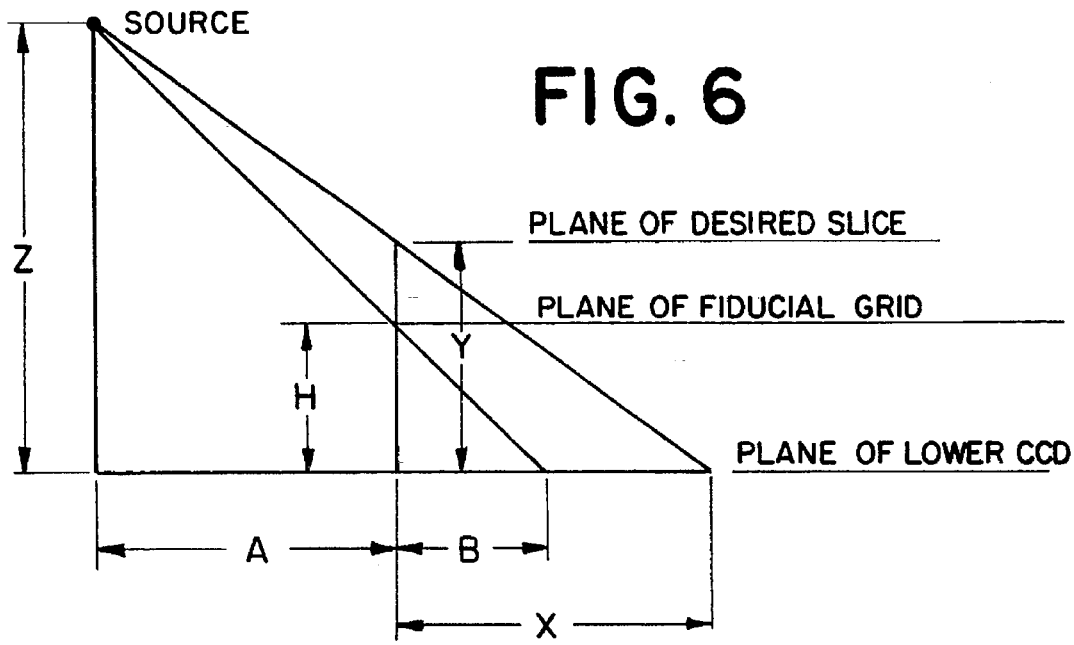
FIG. 6 is a diagram representing relative projection displacement at a finite focal-object distance.

The principle of relative projection displacement is represented in FIG. 6, in which the following variables are depicted:

$Z$=vertical distance between the radiation source and the detector plane of the lower CCD $H$=vertical distance between the plane of the fiducial grid and the detector plane of the lower CCD $Y$=vertical distance between the plane of the desired slice and the detector plane of the lower CCD $A$=horizontal distance along the detector plane between the horizontal position of the radiation source and the horizontal position of an actual fiducial reference point $B$=horizontal displacement along the detector plane between the actual position of the image of the fiducial reference point in the detector plane and the horizontal position of the actual fiducial reference point $X$=horizontal displacement along the detector plane between the expected image position in the detector plane of the fiducial reference point when the actual fiducial reference point is vertically transposed into the desired slice plane and the horizontal position of the actual fiducial reference point From the foregoing descriptions, if F=relative slice position, then F may be defined as follows:

$$F=Y/H$$

If M=magnification of the fiducial reference, then:

$$M=Z/(Z-H)$$

If f(F)=relative projection displacement, then:

$$f(F)=X/B$$

From the following geometric relationships:

$$Y/X=Z/(X+A)$$

and $$H/B=Z/(A+B)$$

the relative projection displacement f(F) can be derived as a function of F and M to be:

$f(F)=F/[M(1-F)+F]$

Accordingly, as set forth in step 102, the relative projection displacement f(F) can be determined from the relative slice position F and the magnification M.

Next, at step 104, magnification of the desired slice is standardized by a correction factor for slice magnification. The magnification correction factor represents a scalar adjustment factor in the relative magnification of the projection of the fiducial reference at a selected slice location. Once again, the computation of relative magnification is beneficial for finite focal-object distances. If the distance from the source of radiation to the fiducial reference grid 50 becomes relatively large with respect to the distance from the fiducial reference grid to the detector plane of the second image detector 42, then relative magnification becomes negligible and may be ignored.

Figure 7:
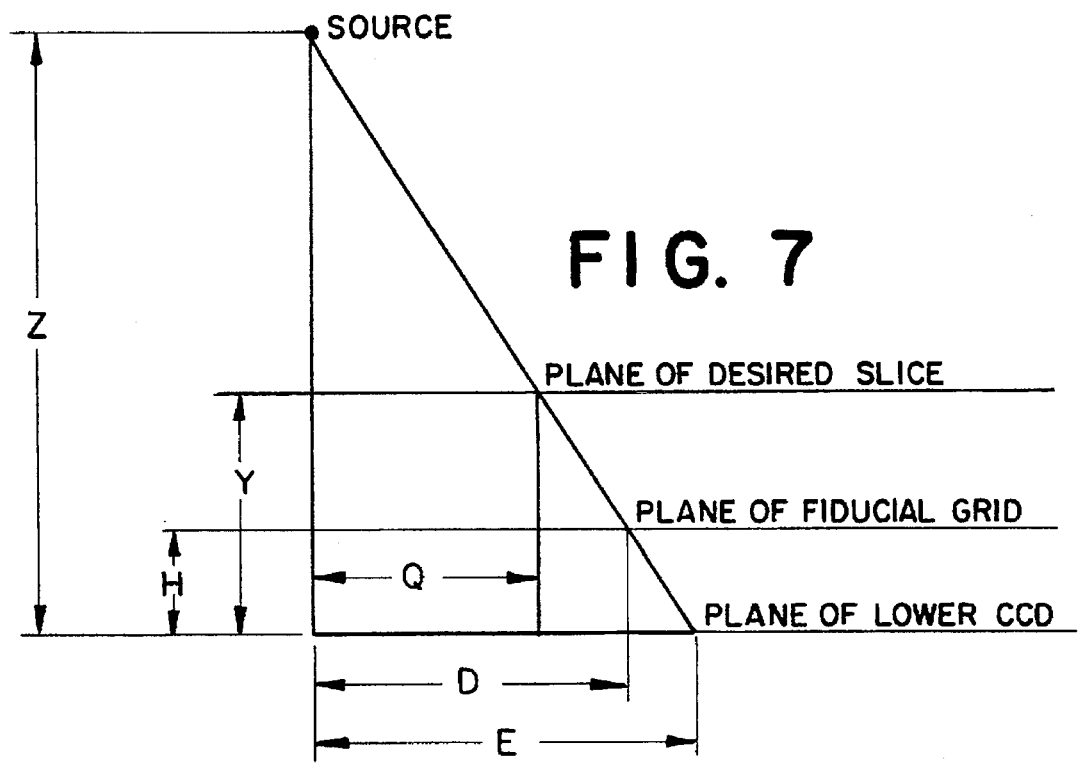
FIG. 7 is a diagram representing relative magnification at a selected slice position for a finite focal-object distance.

The principle for correction of magnification of a selected projection for a particular slice is represented in FIG. 7. The variables Z, H, and Y, depicted in FIG. 7, are the same variables depicted in FIG. 6. With respect to variables Q, D, and E, the following definitions apply:

Q=horizontal distance along the detector plane between the horizontal position of the radiation source and the horizontal position of an expected image location of the fiducial reference point in the plane of the desired slice D=horizontal distance along the detector plane between the horizontal position of the radiation source and the horizontal position of the actual fiducial reference point E=horizontal distance along the detector plane between the horizontal position of the radiation source and the actual position of the image of the fiducial reference point in the detector plane From the foregoing definitions, if F=the relative slice position, then F may be defined as follows:

$F=Y/H$

If M=magnification of the fiducial reference, then M may be defined as follows:

$M=E/D$

If C=the correction factor for slice magnification, then C may be defined as follows:

$C=Q/D$

From the following geometric relationship:

$H/(E-D)=Y/(E-Q)$ the magnification correction factor C can be derived as a function of F and M to be:

$C=M-F(M-1)$

Thus, the magnification correction factor C can be determined from the relative slice position F and the magnification M to enable the magnification of the desired slice to be standardized in step 104.

Next, at step 106, the coordinates of a single pixel located at the respective displacement of each projection of the fiducial reference point to the selected slice position are determined. Referring to FIG. 5 again, the square containing the circular target represents the center of gravity or the point of uniform convergence of the small squares labelled 1 which, in turn, represent the initial locus of projections of the single fiducial reference point in the detector plane.

Intermediate positions of uniform convergence represent ideal positions of the images of the fiducial reference point for selected relative slice positions. For example, for a selected relative slice position of 0.5, the small squares labelled 0.5 indicate the ideal positioning of the respective images of the fiducial reference point. The lined squares with the dark borders correspond to the integer approximations of the respective ideal positions represented by the small squares labelled 0.5 along the dotted lines connecting the initial positions represented by the small squares labelled 1 with the convergent target position. As such, the lined squares with the dark borders represent the respective pixels to which the initial locus of fiducial reference image points would respectively shift for a selected relative slice position of 0.5. The remaining lined squares represent integer approximations to other remaining positions traversed by the connecting lines.

After determination in step 106 of the respective pixels to which each projection of the fiducial reference point should shift for a selected relative slice position, each constituent projection image is then shifted in step 108 such that all associated projections of the fiducial reference point move to their respective pixels at the selected relative slice position. Thus, as shown in FIG. 5, all constituent images would be respectively shifted so that the projections of the fiducial reference point would move to the lined squares with the dark black borders for a selected relative slice position of 0.5. For a selected relative slice position of 1, all projections of the fiducial reference point would coincide at the target position. For a selected relative slice position greater than 1, all projections of the fiducial reference point would uniformly diverge on the opposite side of the target position relative the initial locus.

Next, in step 110, all of the shifted constituent images are spatially averaged. In step 112, the resulting image is optionally filtered in a task-dependent manner. The synthesized image is then displayed in step 114.

As set forth in step 116, if an additional image slice is desired, the process reiterates steps 100 through 114. However, if no additional slices are desired at step 116, the process stops at step 118.

From the foregoing description, it can be seen that a self-calibrating tomosynthetic x-ray system is provided which does not require fixed geometric positioning of the x-ray source relative to the object of interest. In accordance with Applicant's invention, a versatile system is provided having diverse applicability for medical and industrial uses. Accordingly, the present invention is not limited to the particular embodiments described or depicted herein, but is intended to cover all modifications and changes within the scope of the accompanying claims.

What is claimed is:

1. A device for recording radiographic images of a selected object irradiated by a source of radiation comprising:

(a) a support;

(b) a first radiographic recording medium supported on the support for recording a projected radiographic image of the selected object;

(c) a second radiographic recording medium supported relative to the support in fixed position relative to the first radiographic recording medium and at a selected orientation relative to the first radiographic recording medium for recording a projected radiographic image; and (d) a radiopaque fiducial reference supported relative to the support at a fixed position relative to the first and second radiographic recording mediums to permit a projected radiographic image of the radiopaque fiducial reference to be recorded on the second radiographic recording medium wherein the fiducial reference includes a frequency indicator for exhibiting a selected frequency pattern at the fiducial reference.

2. The device in accordance with claim 1 wherein the first radiographic recording medium is radiolucent and is positioned relative to the second radiographic recording medium to permit radiation from the source of radiation to pass through the first radiographic recording medium and impinge upon the second radiographic recording medium.

3. The device in accordance with claim 2 wherein the first radiographic recording medium is positioned generally parallel to the second radiographic recording medium.

4. The device in accordance with claim 3 wherein the radiopaque fiducial reference is positioned intermediate the first and second radiographic recording mediums.

5. The device in accordance with claim 1 wherein the first radiographic recording medium is radiolucent and is positioned relative to the second radiographic recording medium to permit radiation from the source of radiation to pass through the first radiographic recording medium and impinge upon the second radiographic recording medium and wherein the radiopaque fiducial reference is positioned intermediate the first and second radiographic recording mediums to enable the first radiographic recording medium to record a first projected image of the selected object and to enable the second radiographic recording medium to record the projected image of the radiopaque fiducial reference and a second projected image of the selected object.

6. The device in accordance with claim 5 wherein each of the first and second radiographic recording mediums includes a CCD device.

7. The device in accordance with claim 5 wherein said radiopaque fiducial reference includes a radiopaque grid.

8. The device in accordance with claim 7 wherein the first and second recording mediums and the radiopaque grid are oriented generally parallel with one another.

9. The device in accordance with claim 8 wherein each of the first and second radiographic recording mediums includes a CCD device.

10. The device in accordance with claim 1 wherein said frequency indicator exhibits a selected frequency pattern at thhe fiducial reference so that the projected image of the fiducial reference can exhibit a different frequency pattern relative to the frequency pattern exhibited at the fiducial reference.

11. The device in accordance with claim 10 wherein said frequency indicator includes a radiopaque grid.

12. The device in accordance with claim 1 wherein said frequency indicator exhibits a selected frequency pattern at the fiducial reference so that the projected image of the fiducial reference can exhibit a frequency pattern having a phase shift relative to the selected frequency pattern at the fiducial reference.

13. The device in accordance with claim 12 wherein said frequency indicator includes a radiopaque grid.

14. The device in accordance with claim 1 wherein the radiopaque fiducial reference includes a displacement indicator at the fiducial reference for indicating a selected position of the fiducial reference so that the projected image of the fiducial reference can exhibit a displacement to a different position relative to the selected position of the displacement indicator of the fiducial reference.

15. The device in accordance with claim 1 wherein the radiopaque fiducial reference includes a displacement indicator at the fiducial reference for indicating a selected size of the fiducial reference so that the projected image of the fiducial reference can exhibit a different size relative to the selected size of the displacement indicator of the fiducial reference.

16. An apparatus for tomosynthesis of multiple object images of a selected object comprising:
  (a) an image detector positioned at a fixed position relative to the selected object for detecting said multiple object images;
  (b) a fiducial reference positioned at a fixed position relative to the selected object for producing multiple reference images on said image detector to yield composite images of said reference and object images detected upon said image detector; and
  (c) an image synthesizer for analyzing parameters related to positions and sizes of reference images of said composite images detected upon said image detector to produce image translation data, and for reconstructing a tomographic slice from said composite images and said image translation data.

17. The apparatus of claim 16 wherein said fiducial reference includes a metallic bead.

18. The apparatus of claim 16 wherein said image detector includes a CCD device.

19. The apparatus of claim 16 wherein said image detector includes first image detecting medium for recording said multiple object images and a second image detecting medium supported in a fixed position at a selected angle of orientation relative to said first image detecting medium for recording said composite images.

20. The apparatus of claim 19 wherein said fiducial reference is positioned between said first and second image detecting mediums.

21. The apparatus of claim 20 wherein said fiducial reference includes a reference frequency pattern for providing a reference frequency pattern image within said composite image so that said reference frequency pattern image recorded by said second image detecting medium can exhibit a different frequency pattern and a phase shift relative to said reference frequency pattern.

22. The apparatus of claim 21 wherein said parameters related to positions and sizes of the reference images of said composite images detected upon said image detector include said different frequency pattern and said phase shift relative to said reference frequency pattern.

23. The apparatus of claim 21 wherein said reference frequency pattern includes a grid.

24. A system for tomosynthesis of multiple projected object images of a selected object comprising:
  (a) an image detector for detecting multiple projected object images at different relative positions to the selected object;
  (b) a fiducial reference located at a fixed reference position relative to the selected object for producing multiple projected reference images upon said image detector; and
  (c) an image synthesizer for analyzing parameters related to positions and sizes of the reference images detected upon said image detector to produce image translation data, and for reconstructing a tomographic slice from said object images and said image translation data.

25. A method for synthesizing an image of a selected object at a selected slice position through the selected object from a plurality of images of the selected object comprising:
  (a) providing at least one recording means for recording images of the selected object;

(b) providing at least one fiducial reference in fixed position relative to the recording means;

(c) maintaining the selected object in fixed position relative to the recording means and the fiducial reference;

(d) providing at least one imaging source for producing images of the object and the fiducial reference to be recorded on the recording means;

(e) varying the relative positions between (1) the imaging source and (2) the object, the fiducial reference and the recording means;

(f) recording images of the object and the fiducial reference on the recording means at different arbitrary relative positions between (1) the imaging source and (2) the object, the fiducial reference and the recording means; and (g) synthesizing an image of the selected object at a selected slice position through the object from selected images of the object and the fiducial reference recorded on the recording means.

26. The method in accordance with claim 25 wherein the step of varying the relative positions between (1) the imaging source and (2) the object, the fiducial reference, and the recording means includes moving the object, the fiducial reference, and the recording means relative to the imaging source.

27. The method in accordance with claim 26 wherein the step of moving the object, the fiducial reference and the recording means relative to the imaging source includes:

(a) maintaining the imaging source in a fixed position; and (b) placing the object, the fiducial reference and the recording means on a conveyer for moving the object, the fiducial reference and the recording means relative to the imaging source.

28. The method in accordance with claim 26 wherein the step of varying the relative positions between (1) the imaging source and (2) the object, the fiducial reference, and the recording means includes varying the relative positions in an arbitrary manner.

29. The method in accordance with claim 25 wherein the imaging source includes a source of x-ray radiation.

30. The method in accordance with claim 25 wherein the step of varying the relative positions between (1) the imaging source and (2) the object, the fiducial reference, and the recording means includes moving the imaging source relative to the object, the fiducial reference, and the recording means.

31. The method in accordance with claim 25 wherein the step of varying the relative positions between (1) the imaging source an (2) the object, the fiducial refrence, and the recording means includes varying the relative positions in an arbitrary manner.

32. The method in accordance with claim 25 wherein the step of synthesizing an image of the selected object at a selected slice position through the object includes:

(a) selecting the respective recordings of images of the object and the fiducial reference recorded on the recording means for synthesizing the image at the selected slice.

(b) determining for each selected recording the location of the image of the fiducial reference at a plane at the recording means;

(c) selecting a reference location at the plane of the recording means;

(d) determining for each selected recording the distance and path of each recorded image of the fiducial reference from the selected reference location;

(e) determining for each selected recording the respective location of the image of the fiducial reference at the selected slice position such that the position of the image of the fiducial reference for each selected recording will correspond to the selected reference location for a predetermined slice position through the fiducial reference; and (f) shifting for each selected recording the images of the object and the fiducial reference recorded on the recording means to the selected slice position such that the image of the fiducial reference recorded on the recording means for each selected recording moves to its respective location at the selected slice position.

33. The method in accordance with claim 32 including spatially averaging the images of the object and the fiducial reference which have been shifted to the selected slice position.

34. The method in accordance with claim 33 including filtering the spatially averaged images.

35. The method in accordance with claim 32 wherein the reference location at the plane of the recording device is selected as the center of gravity of the images of the fiducial reference recorded on the recording means for the selected recordings.

36. The method in accordance with claim 32 including determining for each selected recording relative displacement of the image of the fiducial reference at the selected slice position.

37. The method in accordance with claim 36 including for each selected recording adjusting the displacement of the image of the object at the selected slice position on the basis of the determined relative displacement.

38. The method in accordance with claim 32 including determining for each selected recordings the magnification of the image of the fiducial reference recorded on the recording means.

39. The method in accordance with claim 38 wherein the magnification is determined by comparing the size of the image of the fiducial reference recorded on the recording means relative to the actual size of the fiducial reference.

40. The method in accordance With claim 38 wherein the fiducial reference includes a frequency indicator for exhibiting a selected frequency pattern at the fiducial reference so that the image of the fiducial reference recorded on the recording means can exhibit a different frequency pattern relative to the frequency pattern exhibited at the fiducial reference and wherein the magnification is determined by comparing the frequency pattern exhibited by the image of the fiducial reference recorded on the recording means with respect to the frequency pattern exhibited at the fiducial reference.

41. The method in accordance with claim 40 wherein the frequency indicator includes a grid.

42. The method in accordance with claim 38 including determining for each selected recording relative magnification of the image of the fiducial reference at the selected slice position based on the determined magnification of the image of the fiducial reference recorded on the recording means.

43. The method in accordance with claim 42 including for each selected recording adjusting the magnification of the image of the object at the selected slice position on the basis of the determined relative magnification.

44. A system for synthesizing an image of a selected object at a selected slice position through the selected object from a plurality of recorded images of the selected object comprising:

(a) at least one recording means for recording images of the selected object;

(b) at least one fiducial reference held in fixed position relative to the recording means;

(c) holder means for holding the recording means and the fiducial reference in fixed position relative to the selected object;

(d) at least one imaging source for producing images of the object and the fiducial reference to be recorded on the recording means;

(e) position varying means for varying the relative positions between (1) the imaging source and (2) the object, the fiducial reference and the recording means so that images of the object and the fiducial reference are recorded on the recording means at different arbitrary relative positions between (1) the imaging source and (2) the object, the fiducial reference and the recording means; and (f) an image synthesizer for synthesizing an image of the selected object at a selected slice position through the object from selected recordings of the images of the object and the fiducial reference recorded on the recording means.

45. The system in accordance with claim 44 wherein the position varying means moves the object, the fiducial reference, and the recording means relative to the imaging source.

46. The system in accordance with claim 45 wherein the position varying means includes a conveyer belt.

47. The system in accordance with claim 44 wherein the imaging source includes a source of radiation.

48. The system in accordance with claim 44 wherein the position varying means varies the relative positions in an arbitrary manner.

49. The system in accordance with claim 44 wherein the image synthesizer includes:

(a) means for determining the location of the image of the fiducial reference at a plane at the recording means for each selected recording of images of the object and the fiducial reference recorded on the recording means;

(b) means for selecting a reference location at the plane of the recording means;

(c) means for determining for each selected recording the distance and path of each image of the fiducial reference from the selected reference location;

(d) means for determining for each selected recording the respective location of the image of the fiducial reference at the selected slice position such that the position of the image of the fiducial reference for each selected recording will correspond to the selected reference location for a predetermined slice position through the fiducial reference; and (e) means for shifting for each selected recording the image of the object and the fiducial reference recorded on the recording means to the selected slice position such that the image of the fiducial reference recorded on the recording means for each selected recording moves so its respective location at the selected slice position.

50. The system in accordance with claim 49 including means for spatially averaging the images of the object which have been shifted to the selected slice position.

51. The system in accordance with claim 49 wherein the reference location at the plane of the recording means is selected as the center of gravity of the images of the fiducial reference recorded on the recording means for the selected recordings.

52. The system in accordance with claim 49 including means for determining the magnification of the image of the fiducial reference recorded on the recording means for each selected recording.

53. The system in accordance with claim 52 wherein the magnification is determined by comparing the size of the image of the fiducial reference recorded on the recording means relative to the actual size of the fiducial reference.

54. The system in accordance with claim 52 wherein the fiducial reference includes a frequency indicator for exhibiting a selected frequency pattern at the fiducial reference so that the image of the fiducial reference recorded on the recording means can exhibit different frequency pattern relative to the frequency pattern exhibited at the fiducial reference and wherein the magnification is determined by comparing the frequency pattern exhibited by the image of the fiducial reference recorded on the recording means with respect to the frequency pattern exhibited at the fiducial reference.

55. The system in accordance with claim 54 wherein the frequency indicator includes a grid.

56. The system in accordance with claim 52 including means for determining for each selected recording relative magnification of the image of the fiducial reference at the selected slice position on the basis of the determined magnification of the image of the fiducial reference recorded on the recording means.

57. The system in accordance with claim 56 including means for adjusting the magnification of the image of the object at the selected slice position on the basis of the determined relative magnification.

58. The system in accordance with claim 49 including means for determining for each selected recording relative displacement of the image of the fiducial reference at the selected slice position.

59. The system in accordance with claim 58 including means for adjusting the displacement of the image of the object at the selected slice position on the basis of the determined relative displacement.

60. A system for synthesizing a tomographic image of a selected object at a selected slice position through the selected object, the system comprising:

(a) a fiducial reference held in a fixed-position relative to the selected object;

(b) an image projector for projecting object images of the selected object and reference images of said fiducial reference;

(c) an image detector located at a fixed position relative to the selected object for detecting said object images and said reference images projected by the image projector; and (d) an image synthesizer for comparing parameters related to positions and sizes of reference images detected upon said image detector to parameters of the fiducial reference to produce image translation data, and for reconstructing the tomographic image from said object images and said image translation data.

61. The system of claim 60 wherein said parameters related to positions and sizes of the reference images detected upon said image detector include a frequency pattern and a phase shift of said detected reference images.

62. The system of claim 60 wherein said image projector comprises a source of radiation.

63. The system of claim 60 wherein said image detector is located for detecting composite images of said object images and said reference images projected by the image projector and wherein said image synthesizer compares parameters related to positions and sizes of the reference images within the composite images to parameters of the fiducial reference to produce the image translation data and wherein the image synthesizer reconstructs the tomographic image from said composite images and said image translation data.

64. A method of tomosynthesis of projected images of a selected object comprising the steps of:

(a) positioning a fiducial reference at a fixed position relative to the selected object;

(b) projecting object images of the selected object and reference images of the fiducial reference;

(c) detecting said projected object images and said projected reference images at a fixed location relative to the selected object to produce image data;

(d) comparing parameters related to positions and sizes of the detected reference images to parameters of the fiducial reference to produce image translation data; and (e) reconstructing a tomographic slice of the selected object from said image translation data and said image data.

65. The method of claim 64 wherein the step of projecting object images and reference images includes projecting composite images of the object images and the reference images and wherein the step of detecting said projected object images and said projected reference images includes detecting said composite images to produce composite image data and wherein the step of reconstructing a tomographic slice includes reconstructing a tomographic slice from said image translation data and said composite image data.

\* \* \* \* \*